US011667976B2

(12) United States Patent
Vogelstein et al.

(10) Patent No.: US 11,667,976 B2
(45) Date of Patent: Jun. 6, 2023

(54) TERT PROMOTER MUTATIONS IN UROTHELIAL NEOPLASIA

(71) Applicant: The Johns Hopkins University, Baltimore, MD (US)

(72) Inventors: Bert Vogelstein, Baltimore, MD (US); Kenneth W. Kinzler, Baltimore, MD (US); Luis Diaz, Ellicott City, MD (US); Nickolas Papadopoulos, Towson, MD (US); George J. Netto, Baltimore, MD (US); Ralph Hruban, Baltimore, MD (US); Isaac A. Kinde, Beaumont, CA (US)

(73) Assignee: The Johns Hopkins University, Baltimore, MD (US)

( * ) Notice: Subject to any disclaimer, the term of this patent is extended or adjusted under 35 U.S.C. 154(b) by 188 days.

(21) Appl. No.: 17/097,510

(22) Filed: Nov. 13, 2020

(65) Prior Publication Data

US 2021/0130908 A1 May 6, 2021

Related U.S. Application Data

(60) Division of application No. 15/077,284, filed on Mar. 22, 2016, now Pat. No. 10,870,890, which is a continuation-in-part of application No. 14/765,692, filed as application No. PCT/US2014/016906 on Feb. 18, 2014, now Pat. No. 10,711,310, application No. 17/097,510 is a continuation of application No. PCT/US2014/051808, filed on Aug. 20, 2014.

(60) Provisional application No. 61/881,113, filed on Sep. 23, 2013, provisional application No. 61/772,249, filed on Mar. 4, 2013, provisional application No. 61/766,857, filed on Feb. 20, 2013, provisional application No. 61/765,909, filed on Feb. 18, 2013.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS 7,879,609 B2  2/2011  Morin et al.

FOREIGN PATENT DOCUMENTS

WO  WO 2012/142213  4/2012

OTHER PUBLICATIONS

U.S. Appl. No. 14/765,692, filed Aug. 4, 2015, Yan et al.
Arita et al., "Upregulating mutations in the TERT promoter commonly occur in adult malignant gliomas and are strongly associated with total 1p19Q loss," Acta Neuropathologica; vol. 126; No. 2, pp. 267-276 (Jun. 14, 2013).
Billerey et al., "Frequent FGFR3 Mutations in Papillary Non-Invasive Bladder (pTa) Tumors," Am J Pathology, 2001, 158: 1955-1959.
Botteman et al., The health economics of bladder cancer: a comprehensive review of the published literature. Pharmaco Economics 2003; 21: 1315-30.
Brimo et al., "Low-grade papillary urothelial carcinoma of the urinary bladder: a clinicopathologic analysis of a post-World Health Organization/International Society of Urological Pathology classification cohort from a single academic center," Archives of pathology & laboratory medicine 2010; 134: 1160-3.
Chaux et al., "High-grade papillary urothelial carcinoma of the urinary tract: a clinicopathologic analysis of a post-World Health Organization/International Society of Urological Pathology classification cohort from a single academic center," Humanpathology 2012; 43: 115-20.
Friedrich et al., "Comparison of multitarget fluorescence in situ hybridization in urine with other noninvasive tests for detecting bladder cancer," BJU international 2003; 92: 911-4.
Friedrich et al., "Detection of methylated apoptosis-associated genes in urine sediments of bladder cancer patients," Clinical Cancer Research; vol. 10; No. 22; pp. 7457-7465 (2004).
Gago-Dominquez et al., "Genetic variations on chromosomes 5p15 and 15q25 and bladder cancer risk: findings from the Los Angeles-Shanghai bladder case-control study," Carcinogenesis, 2010, vol. 32, pp. 197-202.
Herr HW, Donat SM, Reuter VE. Management of low grade papillary bladder tumors. The Journal of urology 2007; 178: 1201-5.
Horn et al., "TERT promoter mutations in familial and sporadic melanoma," Science 2013; 339: 959-61.
Huang et al., "Highly recurrent TERT promoter mutations in human melanoma," Science; vol. 339; No. 6122, pp. 957-959 (Feb. 22, 2013).
International Preliminary Report on Patentability in International Application No. PCT/US2014/051808, dated Mar. 29, 2016.
International Search Report dated Dec. 3, 2014 in corresponding International Application No. PCT/US2014/051808.
International Search Report dated May 26, 2014 in related International Application No. PCT/US2014/016906.
(Continued)

*Primary Examiner* — Sarae L Bausch
(74) *Attorney, Agent, or Firm* — Fish & Richardson P.C.

(57) ABSTRACT

TERT promoter mutations occur in both papillary and flat lesion bladder cancers, are the most frequent genetic alterations identified to date in noninvasive precursor lesions of the bladder, are detectable in urine, and appear to be strongly associated with bladder cancer recurrence. The TERT promoter mutations are useful urinary biomarker for both the early detection and monitoring of bladder neoplasia.

5 Claims, 7 Drawing Sheets

Specification includes a Sequence Listing.

(56) References Cited

OTHER PUBLICATIONS

Kheirollahi et al., "Alterations of telomere length in human brain tumors," Medica Oncology; vol. 28, No. 3, pp. 864-870 (2011).

Killela et al., "TERT promoter mutations occur frequently in gliomas and a subset of tumors derived from cells with low rates of self-renewal," Proceedings of the National Academy of Sciences of the United States of America 2013; 110: 6021-6.

Kinde et al., "Evaluation of DNA from the Papanicolaou test to detect ovarian and endometrial cancers," Sci Transl Med 2013; 5: 167ra4.

Kinde et al., Detection and quantification of rare mutations with massively parallel sequencing. Proceedings of the National Academy of Sciences of the United States of America 2011; 108: 9530-5.

Kinde et al., "TERT promoter mutations occur early in urothelial noplasia and are biomarkers of early disease and dlisease recurrence in urine," Cancer Research; vol. 73; No. 24, pp. 7162-7167(Oct. 11, 2013).

Knowles et al., "Mutation Spectrum of the 9q34 Tuberous Sclerosis Gene TSC1 in Transitional Cell Carcinoma of the Bladder", Cancer Research, Nov. 2003, 63: 7652-7656.

Liu et al., "Highly prevalent TERT promoter mutations in bladder cancer and glioblastoma," Cell Cycle; vol. 12; No. 10, pp. 1637-1638 (May 15, 2013).

Lotan et al., "Sensitivity and specificity of commonly available bladder tumor markers versus cytology: results of a comprehensive literature review and meta-analyses," Urology 2003; 61: 109-18.

Netto et al., "Clinical applications of recent molecular advances in urologic malignancies: no longer chasing a "mirage"?" Advances in anatomic pathology 2013; 20: 175-203.

Oosterhuis et al., "Histological grading of papillary urothelial carcinoma of the bladder: prognostic value of the 1998 WHO/ISUP classification system and comparison with conventional grading systems," Journal of clinical pathology 2002; 55: 900-5.

Roupret (Investigative Urology, BJU, 2008, vol. 101, pp. 1448-1453).

Siegel et al., "Cancer statistics, 2013," CA: a cancer journal for clinicians 2013; 63: 11-30.

Vinagre, "Frequency of TERT promoter mutations in human cancers," Nature Communications, 2013, 4:2185, 6 pages.

Vogelstein et al., "Cancer genome landscapes," Science 2013; 339: 1546-58.

Wu, "Urothelial tumorigenesis: a tale of divergent pathways," Nature Reviews Cancer, 2005, 5: 13-25.

Yan et al., "IDH1 and IDH2 mutations in gliomas," The New England Journal of Medicine; vol. 360; No. 8, pp. 765-773 (2009).

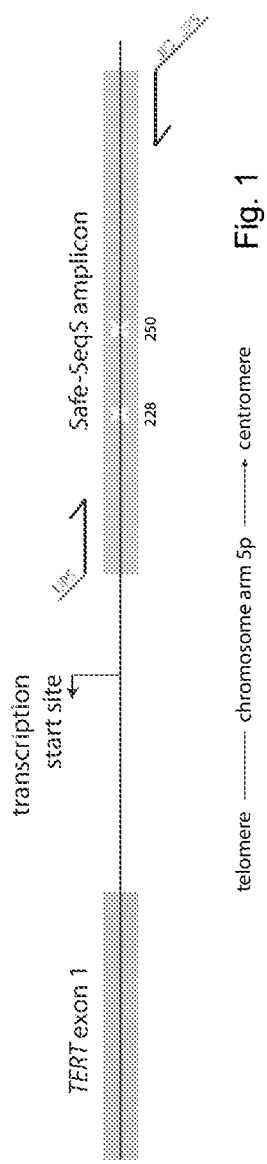

Fig. 2: Table 1: Clinicopathologic characteristics of patients analyzed in this study

|  | pTa LG (N =28)[a] | pTa HG (N =31)[a] | CIS (N =17) | Total |
|---|---|---|---|---|
| Age, mean (range) | 65.5 (46-84) | 67.6 (18-86) | 65.6 (54-80) | 66.4 (18-86) |
| Male, percent | 73% | 84% | 94% | 82% |
| Tumor recurred (%) | 18/28 (64%) | 17/29 (59%) | 11/17 (65%) | 46/68 (68%) |
| Tumor progressed (%) | 6/28 (21%) | 5/29 (17%) | 4/17 (24%) | 15/68 (22%) |
| Follow-up months, median (range) | 56.5 (2-103) | 40 (1-136) | 18 (2-43) | 38 (1-136) |

[a]Recurrence or progression status was not available in two cases. CIS: Carcinoma *in situ*; HG: high-grade noninvasive urothelial carcinoma; LG: low-grade noninvasive urothelial carcinoma; Tumor recurred: tumors recurred within indicated follow-up; Tumor progressed: the recurrent tumor had progressed with respect to stage or grade Fig. 3: Table 2: *TERT* promoter mutations

| *TERT* promoter mutation | pTa LG (N =28) | pTa HG (N =31) | CIS (N =17) | P |
|---|---|---|---|---|
| Present (%) | 24/28 (86%) | 21/31 (68%) | 11/17 (65%) | 0.18 |

CIS: Carcinoma *in situ*; HG: high-grade noninvasive urothelial carcinoma; LG: low-grade noninvasive urothelial carcinoma.

Fig. 4: Table 3: Correlation between *TERT* promoter mutation status and tumor recurrence.

|  | Recurrence on follow-up | Number of patients | *TERT* mutation present (%) | *TERT* mutation absent (%) | P |
|---|---|---|---|---|---|
| pTa LG (N =28)[a] | Yes | 17 | 16/17 (94%) | 1/17 (6.0%) | 0.21 |
|  | No | 9 | 7/9 (78%) | 2/9 (22%) |  |
| pTa HG (N =31)[a] | Yes | 17 | 13/17 (77%) | 4/17 (24%) | 0.14 |
|  | No | 12 | 6/12 (50%) | 6/12 (50%) |  |
| CIS (N =17) | Yes | 11 | 7/11 (64%) | 4/11 (36%) | 0.90 |
|  | No | 6 | 4/6 (67%) | 2/6 (33%) |  |

[a]Recurrence status was not available in two cases. CIS: Carcinoma *in situ*; HG: high-grade noninvasive urothelial carcinoma; LG: low-grade noninvasive urothelial carcinoma.

Fig. 5: Table 4: Correlation of *TERT* promoter mutation status and tumor progression

| | Progression on follow-up | Number of patients | *TERT* mutation present (%) | *TERT* mutation absent (%) | P |
|---|---|---|---|---|---|
| pTa LG | Yes | 6 | 6/6 (100%) | 0/6 (0%) | 0.31 |
| (N =28) | No | 22 | 17/22 (77%) | 3/22 (14%) | |
| pTa HG | Yes | 5 | 4/5 (80%) | 1/5 (20%) | 0.45 |
| (N =31)[a] | No | 24 | 15/24 (63%) | 9/24 (38%) | |
| CIS | Yes | 4 | 3/4 (75%) | 1/4 (25%) | 0.60 |
| (N =17) | No | 13 | 8/13 (62%) | 5/13 (39%) | |

[a]Progression status was not available in two cases. CIS: Carcinoma *in situ*; HG: high-grade noninvasive urothelial carcinoma; LG: low-grade noninvasive urothelial carcinoma; NA: not available.

Fig. 6: Table 5: Correlation of *TERT* mutation status in original diagnostic transurethral resection biopsy (TURB) tissue and *TERT* mutation status in urine collected at follow-up.

| Patient | Original diagnostic TURB mutation (%) | Follow-up urine mutation (%) | Tumor grade | Recurrence at time of urine collection | Recurrence after urine collection |
|---|---|---|---|---|---|
| 1 | g.1295228C>T (11%) | g.1295228C>T (6.3%) | pTa HG | Yes | NA |
| 2 | g.1295250C>T (4.1%) | g.1295250C>T (23%) | pTa HG | Yes | No |
| 3 | g.1295228C>T (5.9%) | g.1295228C>T (0.17%) | pT1 HG | Yes | NA |
| 4 | Absent | Absent | pT1 HG | No | No |
| 5 | Absent | Absent | pT1 HG | No | No |
| 6 | g.1295228C>T (6.7%) | g.1295228C>T (0.64%) | pT1 HG | Yes | NA |
| 7 | g.1295228C>T (8.7%) | g.1295228C>T (4.6%) | pTa LG | Yes | Yes |
| 8 | g.1295228C>T (7.8%) | Absent | pTa HG | No | Yes |
| 9 | g.1295228C>T (7.0%) | Absent | pT1 HG | No | No |
| 10 | g.1295228C>T (5.1%) | Absent | pTa HG | No | NA |
| 11 | g.1295228C>T (4.8%) | Absent | pT1 HG | No | No |
| 12 | g.1295228C>T (5.5%) | g.1295228C>T (5.1%) | pT1 HG | Yes | Yes |
| 13 | Unknown | g.1295228C>T (6.6%) | Unknown | Yes | Yes |
| 14 | Absent | Absent | pTa HG | No | No |
| 15 | g.1295250C>T (23%) | g.1295250C>T (0.69%) | pT1 HG | Yes | Yes |

Genomic coordinates refer to the minus (-) strand of chromosome 5 (hg19 assembly); HG: high-grade noninvasive urothelial carcinoma; LG: low-grade noninvasive urothelial carcinoma; NA: not applicable.

Fig. 7: Table 6: Correlation of *TERT* promoter mutation status in follow-up urine samples with recurrence

| TERT mutation in follow-up urine | Number of patients | Recurred | Did not recur | P |
|---|---|---|---|---|
| Present | 8 | 8/8 (100%) | 0/8 (0%) | <0.001 |
| Absent | 7 | 1/7 (11%) | 6/7 (89%) | $(r = 0.87)$[a] |

[a]Pearson coefficient of correlation

Fig. 8: Table S1. *TERT* promoter mutation status in 59 pTa and 17 carcinoma *in situ* (CIS) patients.

| Patient | TERT promoter mutation | Fraction of mutant alleles | Tumor grade |
|---|---|---|---|
| 1 | g.1295228C>T | 24% | pTa LG |
| 2 | g.1295250C>T | 33% | pTa LG |
| 3 | g.1295228C>T | 24% | pTa LG |
| 4 | g.1295228C>T | 18% | pTa LG |
| 6 | g.1295228C>T | 25% | pTa LG |
| 7 | g.1295228C>T | 29% | pTa LG |
| 8 | g.1295228C>T | 24% | pTa LG |
| 10 | Absent | NA | pTa LG |
| 11 | g.1295228C>T | 24% | pTa LG |
| 12 | g.1295228C>T | 21% | pTa LG |
| 13 | g.1295228C>A | 31% | pTa LG |
| 14 | g.1295250C>T | 40% | pTa LG |
| 15 | g.1295228C>T | 23% | pTa LG |
| 16 | g.1295228C>T | 22% | pTa LG |
| 17 | Absent | NA | pTa LG |
| 18 | g.1295228C>T | 15% | pTa LG |
| 19 | Absent | NA | pTa LG |
| 20 | g.1295250C>T | 31% | pTa LG |
| 21 | g.1295228C>T | 20% | pTa HG |
| 22 | g.1295228C>T | 27% | pTa HG |
| 23 | g.1295228C>T | 30% | pTa HG |
| 24 | Absent | NA | pTa HG |
| 25 | g.1295228C>T | 21% | pTa HG |
| 26 | g.1295228C>T | 4.9% | pTa HG |
| 27 | Absent | NA | pTa HG |
| 28 | g.1295228C>T | 36% | pTa HG |
| 29 | g.1295228C>T | 30% | pTa HG |
| 30 | g.1295228C>T | 32% | pTa HG |
| 31 | Absent | NA | pTa HG |
| 32 | g.1295228C>T | 28% | pTa HG |
| 33 | g.1295250C>T | 50% | pTa HG |
| 34 | g.1295242C>T | 49% | pTa HG |
| 35 | Absent | NA | pTa HG |
| 36 | Absent | NA | pTa HG |
| 37 | g.1295228C>T | 34% | pTa HG |
| 38 | Absent | NA | pTa HG |
| 39 | Absent | NA | pTa HG |
| 40 | g.1295228C>T | 32% | pTa HG |
| 41 | g.1295228C>T | 7.3% | pTa HG |

Fig. 8 (continued)

| | | | |
|---|---|---|---|
| 42 | g.1295228C>T | 11% | CIS |
| 43 | g.1295250C>T | 1.9% | CIS |
| 44 | g.1295250C>T | 4.2% | CIS |
| 45 | g.1295250C>T | 2.1% | CIS |
| 46 | Absent | NA | CIS |
| 47 | g.1295228C>T | 7.7% | CIS |
| 48 | g.1295250C>T | 19% | CIS |
| 49 | g.1295228C>T | 3.3% | CIS |
| 50 | Absent | NA | CIS |
| 51 | g.1295228C>T | 4.3% | CIS |
| 52 | g.1295228C>T | 8.4% | CIS |
| 53 | g.1295228C>T | 6.7% | CIS |
| 54 | Absent | NA | CIS |
| 55 | Absent | NA | CIS |
| 56 | Absent | NA | CIS |
| 57 | g.1295250C>T | 7.5% | CIS |
| 58 | g.1295228C>T | 3.7% | CIS |
| 59 | Absent | NA | pTa LG |
| 60 | g.1295228C>T | 6.7% | pTa HG |
| 61 | g.1295228C>T | 7.0% | pTa LG |
| 62 | Absent | NA | pTa HG |
| 63 | g.1295228C>T | 8.3% | pTa LG |
| 64 | g.1295228C>T | 7.9% | pTa HG |
| 65 | g.1295250C>T | 31% | pTa LG |
| 66 | g.1295250C>T | 23% | pTa HG |
| 67 | g.1295228C>T | 5.4% | pTa LG |
| 68 | Absent | NA | pTa HG |
| 69 | g.1295228C>T | 7.9% | pTa LG |
| 70 | g.1295228C>T | 7.1% | pTa HG |
| 71 | g.1295242C>T | 12% | pTa LG |
| 72 | g.1295250C>T | 24% | pTa HG |
| 73 | g.1295228C>T | 20% | pTa LG |
| 74 | g.1295228C>T | 1.5% | pTa HG |
| 75 | g.1295228C>T | 8.5% | pTa LG |
| 76 | Absent | NA | pTa HG |
| 77 | g.1295228C>T | 9.6% | pTa LG |
| 78 | g.1295228C>T | 6.5% | pTa HG |

Genomic coordinates refer to the minus (-) strand of chromosome 5 (hg19 assembly). CIS: Carcinoma *in situ*; HG: high-grade noninvasive urothelial carcinoma; LG: low-grade noninvasive urothelial carcinoma.

SEQUENCE LISTING

```
<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: TERT promoter and universal priming site or
      unique identifier code

<400> SEQUENCE: 1
cacacaggaa acagctatga ccatgggccg cggaaaggaa g                          41

<210> SEQ ID NO 2
<211> LENGTH: 52
<212> TYPE: DNA
<213> ORGANISM: Artificial Sequence
<220> FEATURE:
<223> OTHER INFORMATION: TERT promoter and universal priming site or
      unique identifier code
<220> FEATURE:
<221> NAME/KEY: misc_feature
<222> LOCATION: (1)...(52)
<223> OTHER INFORMATION: n = A,T,C or G

<400> SEQUENCE: 2
cgacgtaaaa cgacggccag tnnnnnnnnn nnnnncgtcc tgccccttca cc              52

<210> SEQ ID NO 3
<211> LENGTH: 42
<212> TYPE: DNA
<213> ORGANISM: Artificial Sequence
<220> FEATURE:
<223> OTHER INFORMATION: TERT promoter and universal priming site or
      unique identifier code

<400> SEQUENCE: 3
cacacaggaa acagctatga ccatggcgga aaggaaaggg ag                         42

<210> SEQ ID NO 4
<211> LENGTH: 49
<212> TYPE: DNA
<213> ORGANISM: Artificial Sequence
```

```
<220> FEATURE:
<223> OTHER INFORMATION: TERT promoter and universal priming site or
      unique identifier code
<220> FEATURE:
<221> NAME/KEY: misc_feature
<222> LOCATION: (1)...(49)
<223> OTHER INFORMATION: n = A,T,C or G

<400> SEQUENCE: 4
cgacgtaaaa cgacggccag tnnnnnnnnn nnnnnccgtc ccgacccct          49

<210> SEQ ID NO 5
<211> LENGTH: 17
<212> TYPE: DNA
<213> ORGANISM: Homo sapiens

<400> SEQUENCE: 5
gcggaaagga aggggag                                             17

<210> SEQ ID NO 6
<211> LENGTH: 14
<212> TYPE: DNA
<213> ORGANISM: Homo sapiens

<400> SEQUENCE: 6
ccgtcccgac ccct                                                14

<210> SEQ ID NO 7
<211> LENGTH: 16
<212> TYPE: DNA
<213> ORGANISM: Homo sapiens

<400> SEQUENCE: 7
ggccgcggaa aggaag                                              16

<210> SEQ ID NO 8
<211> LENGTH: 17
<212> TYPE: DNA
<213> ORGANISM: Homo sapiens

<400> SEQUENCE: 8
cgtcctgccc cttcacc                                             17
```

TERT PROMOTER MUTATIONS IN UROTHELIAL NEOPLASIA

This invention was made with government support under grants CA043460 and CA057345 awarded by the National Institutes of Health. The government has certain rights in the invention.

The disclosures of prior applications U.S. Ser. No. 61/881,113 filed 23 Sep. 2013, PCT/US14/51808 filed 20 Aug. 2014, U.S. Ser. No. 61/765,909 filed 18 Feb. 2013, U.S. Ser. No. 61/766,857 filed 20 Feb. 2013, U.S. Ser. No. 61/772,249 filed 4 Mar. 2013, PCT/US14/16906 filed 18 Feb. 2014, U.S. Ser. No. 14/765,692 filed 4 Aug. 2015, and U.S. Ser. No. 15/077,284 filed 22 Mar. 2016 are expressly incorporated herein.

TECHNICAL FIELD OF THE INVENTION

This invention is related to the area of cancer. In particular, it relates to urothelial cancers.

BACKGROUND OF THE INVENTION

Urothelial carcinoma of the bladder is the most common malignancy of the urinary tract with 73,000 new cases and 15,000 deaths expected in 2013 in the US alone (1). These invasive carcinomas arise from histologically well-defined papillary and flat precursor lesions, providing a potential opportunity for early detection and treatment (2). Although urine cytology enjoys a reasonable sensitivity and specificity for detecting high-grade neoplasms, its performance in detecting low-grade tumors is poor, with a sensitivity and specificity of 4% and 30%, respectively (3).

A number of urine-based markers have been developed to improve the accuracy of noninvasive screening and surveillance in bladder cancer. Among Food and Drug Administration (FDA) approved tests, the Immunocy test (Scimedx Corp, Danville, N.J.), nuclear matrix protein 22 (NMP22) immunoassay test (Matritech, Cambridge, Mass.) and multitarget fluorescence in situ hybridization (FISH) (UroVysion; Abbott Park, Ill.) (4) have demonstrated an overall sensitivity of 70% and a specificity range of up to 89%. Performance inconsistencies, as a result of variability in pre-analytical and analytical specimen factors, have impeded their wide-spread clinical use.

Activating mutations in the promoter of the telomerase reverse transcriptase (TERT) gene lead to increased telomerase expression and, in doing so, allow some neoplasms to overcome the end-replication problem and avoid senescence. TERT promoter mutations were initially described in melanoma (5, 6) and have subsequently been described in a discrete spectrum of cancer types, including 66% of muscle-invasive urothelial carcinomas of the bladder (5, 7). TERT is therefore the most frequently mutated gene in advanced forms of this disease, and the localization of these mutations to a small gene region in the TERT promoter provides an extraordinary opportunity for biomarker development (7).

Muscle-invasive urothelial carcinoma is responsible for the vast majority of bladder cancer related deaths and many of these deaths could be prevented if precursor lesions were detected and surgically excised prior to their invasion into the muscle (10-13). New strategies for the early detection of such lesions are therefore urgently needed (14). There is a continuing need in the art to find ways of detecting early, curable, bladder disease and for monitoring recurrences of bladder cancer after tumor resection.

SUMMARY OF THE INVENTION

According to one embodiment of the invention a method is provided. Nucleic acids obtained from a urine sample of a human are tested for a genetic alteration in telomerase reverse transcriptase promoter at one or more nucleotides between 1295205 and 1295297 on the minus strand of chromosome 5 in version hg19 of human genome sequence. The human has not been diagnosed with bladder cancer.

According to another aspect of the invention a method is provided. Nucleic acids obtained from a urine sample of a patient are tested for a genetic modification in telomerase reverse transcriptase promoter. One or more nucleotides between 1295205 and 1295297 on the minus strand of chromosome 5 in version hg19 of human genome sequence are interrogated. The patient has had a surgical excision or other treatment for a bladder cancer.

Another aspect of the invention is two primer pairs. In the first pair, a first primer comprises a first segment of TERT promoter region gcggaaaggaagggag (SEQ ID NO: 5), and a second primer comprises a second segment of TERT promoter region CCGTCCCGACCCCT (SEQ ID NO: 6). In the second pair, a first primer comprises a first segment of TERT promoter region ggccgcggaaaggaag (SEQ ID NO: 7), and a second primer comprises a second segment of TERT promoter region CGTCCTGCCCCTTCACC (SEQ ID NO: 8).

These and other embodiments which will be apparent to those of skill in the art upon reading the specification provide the art with

BRIEF DESCRIPTION OF THE DRAWINGS

FIG. 1 shows a schematic of the TERT locus and positioning of the Safe-SeqS amplification primers. The yellow marks indicate the positions (offset by −1,295,000 base pairs) of the most common TERT promoter mutations previously reported and identified in this study. UID: Unique identifier; UPS: Universal primer binding site.

FIG. 2=Table 1: Clinicopathologic characteristics of patients analyzed in this study FIG. 3=Table 2: TERT promoter mutations FIG. 4=Table 3: Correlation between TERT promoter mutation status and tumor recurrence.

FIG. 5=Table 4: Correlation of TERT promoter mutation status and tumor progression FIG. 6=Table 5: Correlation of TERT mutation status in original diagnostic transurethral resection biopsy (TURB) tissue and TERT mutation status in urine collected at follow-up.

FIG. 7=Table 6: Correlation of TERT promoter mutation status in follow-up urine samples with recurrence FIG. 8=Table S1. TERT promoter mutation status in 59 pTa and 17 carcinoma in situ (CIS) patients.

DETAILED DESCRIPTION OF THE INVENTION

The inventors have developed a method for detecting TERT promoter mutations in urine. The presence of these mutations in urine is strongly associated with bladder cancer recurrence in patients who have had their tumors removed surgically. Moreover, TERT promoter mutations are the most common genetic alteration in noninvasive bladder cancer identified to date, occurring in the majority (74%) of such precursor lesions. They occur in cancers developing through both the papillary and flat routes to tumor progression (15), and occur in low-grade as well as high-grade tumors. These mutations can be detected in the urine of patients with bladder cancer using sensitive techniques we have developed. TERT promoter mutations provide a useful biomarker for the early detection of bladder cancers, and patients at high risk for this disease can be screened in this noninvasive way.

Given the high prevalence of TERT promoter mutations in early bladder neoplasia, their presence or absence in tumors is of limited prognostic value. However, superficial bladder cancers are currently the most costly solid tumor (per patient) in the U.S. (16, 17). Noninvasive methods to monitor these patients could reduce the cost of caring for these patients as well as the discomfort associated with invasive procedures. Among patients with TERT mutations in their primary tumors, there was a highly significant correlation between the presence of mutations in subsequent urine collections and recurrence (Table 6).

Our results therefore indicate two avenues for application of TERT promoter mutations in the clinic: early detection in high-risk patients and monitoring of patients with bladder cancer, both through the analysis of urine specimens. TERT promoter mutations occur early, are specific for neoplasia, and can be identified in the urine with techniques such as those described below.

Testing nucleic acids can be accomplished by any means known in the art for determining a nucleotide identity at one or more positions. Testing typically involves isolation of nucleic acids from a clinical sample and doing at least one transformative reaction on the nucleic acids. Alternatively, a sample can be treated to make its nucleic acids accessible to probes, to perform an in situ assay. For example, the nucleic acids can be denatured and hybridized to a probe. The nucleic acids can be amplified. The nucleic acids can be hybridized to a primer and the primer extended by one or more bases. The nucleic acids can be modified by an enzyme that uses DNA as a substrate. Each of these methods involves a transformation of nucleic acids. The nucleic acids are a physical substance and are not a representation. One or both strands can be tested or assayed.

Therapies which can be prescribed are any that are known in the art for treating bladder cancer. These may include Bacillus Calmette-Guérin (BCG) and intravesical chemotherapy. Adjuvant therapies may include chemotherapy agents such as cisplatin and gemcitabine. Other chemotherapy agents or biological agents can be used in combination or separately. Similarly, radiation can be used alone or together with other therapies. Prescribing a therapy typically involves a medical professional making a determination based on fact or surmise that a particular therapy will be or might be efficacious. The medical professional typically permanently records this determination in a medical chart or file. In addition, the drug and dosage are reduced to a verbal communication, such as a writing, a voice recording, or an electronic message that is delivered to a dispensing pharmacy.

Any confirmatory test can be performed as is known in the art if a bladder cancer is detected by means of the urine test. One such test is a cytoscopy. Any test that can sensitively detect a bladder cancer can be used.

Elevated risk of a bladder cancer can be ascertained based on known exposure to a carcinogen. Such exposures may be, for example, environmental, nutritional, or pharmaceutical. Cigarette or other tobacco smoking or ingesting, which may be considered an environmental exposure, is a major risk factor. Alternatively or in addition, the elevated risk may be due to a family history of bladder cancer.

Primers according to the invention are complementary to portions of the TERT promoter region. Preferably the primer will comprises a sequence according to any of SEQ ID NOs: 5, 6, 7, or 8. Primers will typically be at least 14, 15, 16, 17, 18, 19, 20, or 21 nucleotides in length and typically will be less than 50, 45, 40, 35, 30, 25 nucleotides in length. The primers will also comprise sequences that are not complementary to portions of the TERT promoter. Thus any of the specified TERT promoter sequences will be linked to other non-TERT promoter sequences. For example, the TERT promoter sequences may be linked to a universal priming site (UPS) and/or a unique identifier (UID). The UID may, for example be comprised of a number of degenerate N bases (equal likelihood of being an A, C, T, or G). The degenerate bases may range from 4-20, typically. Thus the sequence of the primers is not naturally occurring. In some circumstances, the primer may be linked to a non-nucleotide moiety, such as to a fluor, a chromophor, or a radioactive moiety.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods
Patient Samples

This study was approved by the Institutional Review Board of Johns Hopkins University, School of Medicine. Two different sets of samples were analyzed in our study. The first sample set included 76 noninvasive papillary urothelial carcinomas and flat carcinoma in situ (CIS) lesions obtained by transurethral bladder resection (TURB) between 2000 and 2012. All specimens were rom the Surgical Pathology archives and were selected only on the basis of specimen availability. Pertinent patient demographics and clinical information were obtained from electronic medical records. All sections were reviewed by three urological pathologists (EM, SFF and GJN) to confirm the original diagnoses. To enrich for neoplastic cells within the tissues, representative formalin-fixed paraffin-embedded (FFPE) blocks were cored with a sterile 16 gauge needle and tumor areas showing at least 50% neoplastic cellularity were selected microscopically. For eight of the cases, benign adjacent urothelium was macrodissected from FFPE blocks. The cores were placed in a 1.5 mL sterile tube for subsequent DNA purification using an AllPrep DNA/RNA Mini Kit (Qiagen, cat. no. 80204). DNA was purified from peripheral blood buffy coats of 15 patients using the same Qiagen kit.

For the second sample set, we prospectively collected urine samples from 15 separate patients undergoing follow-up cystoscopy for previously diagnosed non-muscle-invasive urothelial carcinoma. We purposely biased this cohort to include patients that recurred within the follow-up period. Immediately prior to follow-up cystoscopy, 25 mL of raw urine was collected and subsequently pelleted by centrifugation at 3,000 g for 10 minutes. The pellets were stored at −80° C. in 1.5 mL tubes for subsequent DNA extraction. For 14 of these patients, matched FFPE from the original diagnostic TURB was retrieved. These included 13 high-grade urothelial carcinomas (pTa HG and pT1 HG in six and seven cases, respectively), and one low-grade papillary urothelial carcinoma (pTa LG). Twenty 8 µm-thick sections were cut from one representative tissue block in each case and areas containing at least 70% neoplastic cells were microdissected and used for DNA purification using a QIAamp DNA FFPE Tissue Kit (Qiagen, cat no. 56404).

Mutation Analysis

Due to their tremendous throughput, massively parallel sequencing instruments are highly cost-effective for DNA mutation analysis. However, sample preparation and sequencing steps introduce artifactual mutations into analyses at a low, but significant frequency. To better discriminate genuine TERT promoter mutations from artifactual sequencing variants introduced during the sequencing process, we used Safe-SeqS, a sequencing error-reduction technology described previously (8, 9). As depicted in FIG. 1, Safe-SeqS amplification primers were designed to amplify a 126-bp segment containing the region of the TERT promoter previously shown to harbor mutations in melanomas and other tumors (5-7). The forward and reverse amplification primers contained the TERT-specific sequences at their 3' ends and a universal priming site (UPS) at their 5' end. The reverse primer additionally contained a 14-base unique identifier (UID) comprised of 14 degenerate N bases (equal likelihood of being an A, C, T, or G) between the UPS and gene-specific sequences. The sequences of the forward and reverse primers were either 5'-CACACAGGAAACAGCTATGACCATGGGCC-GCGGAAAGGAAG (SEQ ID NO: 1) and 5'-CGACGTAAAACGACGGCCAGTNNNNNNNNNN-NNNNCGTCCTGCCCCTTCACC (SEQ ID NO: 2), or 5'-CACACAGGAAACAGCTATGACCATGGCGGAAA-GGAAAGGGAG (SEQ ID NO: 3) and 5'-CGACGTAAAACGACGGCCAGTNNNNNNNNNN-NNNCCGTCCCGACCCCT (UPS sequences underlined; SEQ ID NO: 4). These primers were used to amplify DNA in 25 µL PCR reactions in 1× Phusion Flash High-Fidelity PCR Master Mix (Thermo Scientific, cat. no. F-548L) containing 0.5 µM forward and reverse primers (described above). After incubation at 98° C. for 120 seconds, 10 cycles of PCR were performed in the following manner: 98° C. for 10 seconds, 63° C. for 120 seconds, and 72° C. for 120 seconds was performed. Reactions were purified with AMPure XP beads (Beckman Coulter) and eluted in 100 µL of Buffer EB (Qiagen, cat. no. 19086). For the second stage of amplification, 5 µL of purified PCR products were amplified in 25 µL reactions containing 1× Phusion Flash High-Fidelity PCR Master Mix and 0.5 µM amplification primers that each contained the first-stage UPS at their 3' ends and the grafting sequences required to hybridize to the sequencing instrument flow cell at their 5' ends (8, 9). The reverse amplification primer additionally included a 6 bp index sequence, unique to each sample, inserted between the UPS and grafting sequences. After incubation at 98° C. for 120 seconds, 17 cycles of PCR were performed in the following manner: 98° C. for 10 seconds, 63° C. for 120 seconds, and 72° C. for 120 seconds. The PCR products were purified with AMPure and sequenced on a MiSeq instrument.

Data were analyzed as previously described (8, 9). Briefly, the amplified TERT promoter region of reads containing UIDs, where each base of the UID region had instrument-derived quality scores ≥15, was matched to a reference sequence using a custom script. TERT promoter sequences with five or fewer mismatches were retained for further analysis. Tumor samples were considered positive if the fraction of mutations exceeded 1% of alleles (which was a frequency at least 10× higher than found in control DNA templates from FFPE tissues). Urine samples were considered positive when the frequency of mutation exceeded 0.1% of alleles (a frequency at least 10× higher than found in control DNA templates from urine samples of patients without TERT mutations in their primary tumors). All sequencing assays scored as positive were confirmed in at least one additional, independent PCR and sequence assay.

Statistical Analysis

The data were analyzed using Stata/SE 12 (StataCorp Inc., College Station, Tex.). Pearson's chi-squared test was used for analysis of association of categorical variables. A two-tailed probability <0.05 was required for statistical significance.

Example 2

TERT Promoter Mutation in Papillary and "Flat" Noninvasive Urothelial Carcinoma

We used a massively parallel sequencing technology to determine the presence and representation of mutant TERT promoter alleles in urothelial cancers. A graphical depiction of the method is shown in FIG. 1 and detailed procedures are provided in the Materials and Methods. In addition to revealing whether mutations are present with a population of DNA templates, this technique provides an accurate determination of the fraction of mutant alleles in the sample. Clinicopathologic characteristics of the 76 noninvasive urothelial carcinomas analyzed in the first phase of this study are summarized in Table 1. They included 59 papillary tumors—28 low-grade (pTa LG) and 31 high-grade (pTa HG) —plus 17 "flat" urothelial carcinoma in situ (CIS). These patients were typical of those with this form of cancer; their average age was 66 years and most (82%) were males (Table 1).

TERT promoter mutations were identified in 56/76 (74%) of these urothelial carcinomas (Table 2). In contrast, none of the eight samples of adjacent normal urothelium harbored TERT promoter mutations. Additionally, we did not detect TERT promoter mutations in 15 samples of peripheral blood from the same patients. Twelve of the blood samples and five of the normal urothelial samples were from patients whose tumors harbored TERT promoter mutations. These data demonstrate that the TERT promoter mutations in these patients were unequivocally somatic and limited to the neoplastic urothelium in the bladder. The predominant alterations were g.1295228C>T (minus strand of chromosome 5, hg19 assembly) and g.1295250C>T mutations, which accounted for 75% and 20% of the total alterations, respectively. In addition, we identified one g.1295228C>A mutation and two g.1295242C>T mutations not previously reported (Table S1). The mutations were found in all types and grades of these early cancers: in 76% of papillary lesions and 65% of flat lesions; in 86% of low-grade and in 68% of high-grade lesions (Table 2). None of these differences among subgroups were statistically significant.

The results described above show that TERT promoter mutations occur early in bladder cancers and did not correlate with grade or type. Such early mutations would not be likely associated with recurrence or progression, but to evaluate this possibility, our series of samples included cases both with and without recurrence during follow up. In Tables 3 and 4, the relationship between TERT promoter mutation status and tumor recurrence or progression, respectively, are displayed: TERT promoter mutation status was not associated with likelihood of recurrence or progression in any subgroup.

Example 3

TERT Promoter Mutation in Urine Samples

We next evaluated whether TERT promoter mutations could be identified in cells in the urine. As noted in the Introduction, urine samples are routinely taken at follow-up visits following TURB procedures to help determine whether residual tumor cells are present (via cytology or other methods). We first assessed the tumors obtained from 14 patients undergoing TURB for relatively early (non-muscle invasive) disease. Of these, 11 (79%) harbored TERT promoter mutations (Table 5), as expected from the evaluation of the first cohort (Table 2). All of the mutations in the second cohort were at either g.1295228C>T or g.1295250C>T (Table 5).

The 14 patients were monitored for recurrence at subsequent visits. Mutations were assessed in the cell pellets from the urines obtained at the first follow-up visit after TURB in these 14 patients, as described in the Materials and Methods. There was a striking correlation between the presence of a TERT promoter mutation in the urine, the presence of the mutation in the original tumor, and recurrence. In the three of 14 patients without a TERT promoter mutation in their tumor, no mutation was evident in their urine sample, as expected (Table 5). Of the 11 patients in whom a TERT mutation was present in the tumor, seven patients were observed to have a mutation in the DNA isolated from their urine cell pellets; in each case, the mutation was identical to that observed in the primary tumor removed via TURB (Table 5). The bladder cancers in each of these seven patients recurred, either at the first follow-up or thereafter. The proportion of mutant alleles in the cells pelleted from the urine of these patients was often substantial, ranging from 0.17% to 23% with a median of 4.4% (Table 5). We also identified a TERT promoter mutation in a urine sample from which no prior tumor was available; this tumor also recurred (Table 5). In contrast, no TERT mutations were evident in the urine samples of four patients whose original tumors contained a TERT promoter mutation: the tumors of three of these patients never recurred while the fourth developed a recurrence 3.5 months after the urine sample was collected (Table 5). As shown in Table 6, the presence of detectable TERT promoter mutations in the urine was strongly associated with recurrence of urothelial carcinoma ($P<0.001$; Pearson's correlation coefficient=0.87).

Example 4

TERT Promoter Mutation in Fixed Urine Samples

Following routine cytopathology microscopic examination of urine samples (standard of care in primary screen and surveillance for patients with bladder cancern), a residual portion of the urine samples were kept in the SurePath® preservative. SurePath® Preservative (Becton Dickinson) is an alcohol-based, preservative fluid. The preservation solution serves as a transport, preservative and antibacterial medium for gynecologic (and urine cytology) specimens.

We tested a total of 163 SurePath®-preserved urine specimens. We tested for TERT promoter mutations in 154 urine SurePath® samples, in addition to those described above in Example 3.
The results were as follows:
TERT Mutation Status in Primary Screen Vs. Surveillance Patients:
Primary Screen (Hematuria No Prior Bladder Cancer Diagnosis)
59 Urine SurePath® samples total
21 TERT promoter mutation positive (36%)
31 TERT promoter mutation negative (53%)
7 Borderline TERT promoter mutation
Surveillance Patients (on Follow-Up after a Diagnosis of Bladder Cancer)
94 samples total
55 TERT promoter mutation positive (59%)
31 TERT promoter mutation negative (33%)
8 Borderline TERT promoter mutation As expected, a higher proportion of TERT promoter mutation is encountered in patients with prior diagnosis of bladder cancer (surveillance) compared to those who never had a prior diagnosis of bladder cancer and who are screened for cancer due to a clinical finding hematuria (primary screen).

TERT Promoter Mutation Status Vs. Routine Cytology Microscopy Diagnosis

All urine cytology samples with positive cytology diagnosis were either positive for TERT promoter mutation (14/17; 82%) or borderline positive for TERT promoter mutation (3/14; 18%)

Among 54 urine specimens that had atypical cytology diagnosis 55% were TERT promoter mutation positive; 7% were TERT promoter mutation borderline positive and 38% were negative for TERT promoter mutation Among 80 urine specimens with a negative cytology diagnosis 40% were positive for TERT mutation, 9% were borderline for TERT promoter mutation, and 51% were negative for TERT promoter mutation.

As one would expect, the rate of TERT positivity was higher in patients who had a positive diagnosis by cytology, compared to those who had atypical diagnosis by cytology. The rate of TERT promoter mutation positivity was in turn higher in patients with a diagnosis of atypical cytology compared to those that were negative on cytologic exam.

Among all TERT promoter mutation negative samples, none (0%) were diagnosed as positive on cytology. 67% were negative on cytology, 32% were diagnosed as atypical and one was unsatisfactory for examination by cytology.

REFERENCES

The disclosure of each reference cited is expressly incorporated herein.

1. Siegel R, Naishadham D, Jemal A. Cancer statistics, 2013. CA: a cancer journal for clinicians 2013; 63: 11-30.
2. Netto G J. Clinical applications of recent molecular advances in urologic malignancies: no longer chasing a "mirage"? Advances in anatomic pathology 2013; 20: 175-203.
3. Lotan Y, Roehrborn C G. Sensitivity and specificity of commonly available bladder tumor markers versus cytology: results of a comprehensive literature review and meta-analyses. Urology 2003; 61: 109-18.
4. Friedrich M G, Toma M I, Hellstern A, et al. Comparison of multitarget fluorescence in situ hybridization in urine with other noninvasive tests for detecting bladder cancer. BJU international 2003; 92: 911-4.
5. Horn S, Figl A, Rachakonda P S, et al. TERT promoter mutations in familial and sporadic melanoma. Science 2013; 339: 959-61.
6. Huang F W, Hodis E, Xu M J, Kryukov G V, Chin L, Garraway L A. Highly recurrent TERT promoter mutations in human melanoma. Science 2013; 339: 957-9.
7. Killela P J, Reitman Z J, Jiao Y, et al. TERT promoter mutations occur frequently in gliomas and a subset of tumors derived from cells with low rates of self-renewal.

Proceedings of the National Academy of Sciences of the United States of America 2013; 110: 6021-6.
8. Kinde I, Wu J, Papadopoulos N, Kinzler K W, Vogelstein B. Detection and quantification of rare mutations with massively parallel sequencing. Proceedings of the National Academy of Sciences of the United States of America 2011; 108: 9530-5.
9. Kinde I, Bettegowda C, Wang Y, et al. Evaluation of DNA from the Papanicolaou test to detect ovarian and endometrial cancers. Sci Transl Med 2013; 5: 167ra4.
10. Oosterhuis J W, Schapers R F, Janssen-Heijnen M L, Pauwels R P, Newling D W, ten Kate F. Histological grading of papillary urothelial carcinoma of the bladder: prognostic value of the 1998 WHO/ISUP classification system and comparison with conventional grading systems. Journal of clinical pathology 2002; 55: 900-5.
11. Herr H W, Donat S M, Reuter V E. Management of low grade papillary bladder tumors. The Journal of urology 2007; 178: 1201-5.
12. Miyamoto H, Brimo F, Schultz L, et al. Low-grade papillary urothelial carcinoma of the urinary bladder: a clinicopathologic analysis of a post-World Health Organization/International Society of Urological Pathology classification cohort from a single academic center. Archives of pathology & laboratory medicine 2010; 134: 1160-3.
13. Chaux A, Karram S, Miller J S, et al. High-grade papillary urothelial carcinoma of the urinary tract: a clinicopathologic analysis of a post-World Health Organization/International Society of Urological Pathology classification cohort from a single academic center. Human pathology 2012; 43: 115-20.
14. Vogelstein B, Papadopoulos N, Velculescu V E, Zhou S, Diaz L A, Jr., Kinzler K W. Cancer genome landscapes. Science 2013; 339: 1546-58.
15. Wu X R. Urothelial tumorigenesis: a tale of divergent pathways. Nature reviews Cancer 2005; 5: 713-25.
16. Botteman M F, Pashos C L, Redaelli A, Laskin B, Hauser R. The health economics of bladder cancer: a comprehensive review of the published literature. PharmacoEconomics 2003; 21: 1315-30.
17. Eble J N, Sauter G, Epstein J I. Pathology and Genetics of Tumours of the Urinary System and Male Genital Organs. Lyon, France: International Agency for Research on Cancer Press; 2004.

We claim:

1. A method of treating a human for bladder cancer, comprising:
   determining the presence of at least one somatic mutation in a promoter of a telomerase reverse transcriptase (TERT) gene from a sequenced nucleic acid that was obtained from a urine sample from a human,
   wherein the at least one somatic mutation is C250T at position 1,295,250 on the minus strand of chromosome 5 of version hg19 of the human genome sequence, and
   treating the human subject with the at least one somatic mutation in the TERT gene for bladder cancer by a therapy chosen from: a chemotherapy, a biological agent, or a radiation therapy.

2. The method of claim 1, wherein the human has a transitional cell carcinoma of the urothelial tract.

3. The method of claim 1, wherein the human has no previously detected bladder cancer prior to collection of the urine sample from the human.

4. The method of claim 1, wherein the human has been diagnosed with bladder cancer prior to collection of the urine sample from the human.

5. The method of claim 1, wherein a bladder cancer has been removed from the human prior to collection of the urine sample from the human.

* * * * *

UNITED STATES PATENT AND TRADEMARK OFFICE
CERTIFICATE OF CORRECTION

PATENT NO. : 11,667,976 B2
APPLICATION NO. : 17/097510
DATED : June 6, 2023
INVENTOR(S) : Bert Vogelstein et al.

It is certified that error appears in the above-identified patent and that said Letters Patent is hereby corrected as shown below:

On the Title Page

Item (60) In "Related U.S. Application Data", Column 1, please delete "17/097,510" and insert -- 15/077,284 --.

Item (56) In "Other Publications", Column 2, Line 19, please delete "/Intemational" and insert -- /International --.

Signed and Sealed this
Eighth Day of August, 2023

Katherine Kelly Vidal
*Director of the United States Patent and Trademark Office*